(12) United States Patent
Cuypers et al.

(10) Patent No.: US 10,081,889 B2
(45) Date of Patent: Sep. 25, 2018

(54) HYBRID FABRIC

(75) Inventors: Steven Cuypers, Gravenwezel (BE); Bogdan Bogdanov, Borgerhout (BE)

(73) Assignee: ORFIT INDUSTRIES, Wijnegem (BE)

( * ) Notice: Subject to any disclaimer, the term of this patent is extended or adjusted under 35 U.S.C. 154(b) by 1269 days.

(21) Appl. No.: 12/212,124

(22) Filed: Sep. 17, 2008

(65) Prior Publication Data
US 2009/0075542 A1    Mar. 19, 2009

(30) Foreign Application Priority Data

Sep. 17, 2007   (EP) ..................................... 07116578

(51) Int. Cl.
| | | |
|---|---|---|
| *D03D 15/00* | (2006.01) | |
| *D04B 1/16* | (2006.01) | |
| *A61F 13/04* | (2006.01) | |
| *A61L 15/12* | (2006.01) | |
| *A61L 15/14* | (2006.01) | |
| *A61F 13/00* | (2006.01) | |

(52) U.S. Cl.
CPC ................ *D04B 1/16* (2013.01); *A61F 13/04* (2013.01); *A61L 15/12* (2013.01); *A61L 15/14* (2013.01); *A61F 2013/00238* (2013.01); *D10B 2401/062* (2013.01); *D10B 2509/024* (2013.01); *Y10T 442/30* (2015.04)

(58) Field of Classification Search
CPC ... A61F 2013/00238; D04B 1/16; D04B 1/12; D04B 1/14; D04B 21/104; D04B 21/108; D04B 21/12; D04B 21/14; D04B 21/16; D04B 21/165; D10B 2401/062; D10B 2509/024

USPC ................................................. 442/304–326
See application file for complete search history.

(56) References Cited

U.S. PATENT DOCUMENTS

| | | | | |
|---|---|---|---|---|
| 4,286,586 A | * | 9/1981 | Potts ........................ | A61F 13/04 |
| | | | | 427/2.1 |
| 4,594,283 A | * | 6/1986 | Ohigashi ........................ | 428/218 |
| 5,731,062 A | * | 3/1998 | Kim et al. ..................... | 428/175 |

(Continued)

FOREIGN PATENT DOCUMENTS

| | | |
|---|---|---|
| EP | 0758693 A1 | 2/1997 |
| EP | 0887451 A2 | 12/1998 |

(Continued)

*Primary Examiner* — Elizabeth M Cole
(74) *Attorney, Agent, or Firm* — Sughrue Mion, PLLC

(57) ABSTRACT

This invention relates to a hybrid fabric comprising at least one structural fiber having a first melting temperature range and at least one thermo-formable fiber of having a second melting temperature range which is lower than the first melting temperature range to such an extent that the structural fiber does not melt in the second melting temperature range of the thermo-formable fiber. The hybrid fabric comprises (1) a first network comprising the structural fibers, (2) a second network comprising the thermo-formable fibers, the thermo-formable fibers comprising non-relaxed fibers made of a thermoplastic material, and (3) a plurality of openings between the fibers of the first and second network. The structural and thermo-formable fibers of respectively the first and second network interpenetrate one another and are connected to each other over at least part of the first and second network at a plurality of knot positions in the fabric where the structural and thermo-formable fibers are interwoven.

11 Claims, 1 Drawing Sheet

(56) References Cited

Figure 1:
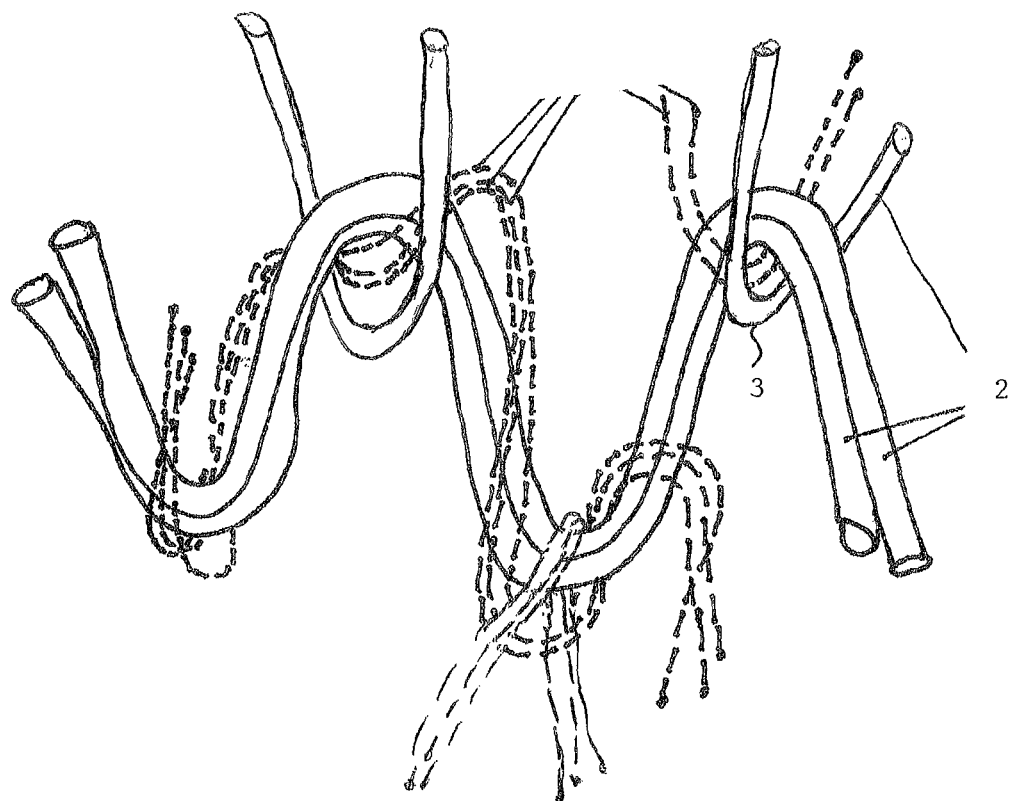

U.S. PATENT DOCUMENTS 5,792,555 A * 8/1998 Bak et al. .................... 428/373
5,888,609 A * 3/1999 Karttunen et al. ............ 428/107

FOREIGN PATENT DOCUMENTS

EP        1582187  A1   10/2005
WO     2005052235  A1    6/2005

* cited by examiner

HYBRID FABRIC

The present invention relates to a hybrid fabric comprising at least one structural fiber having a first melting temperature range and at least one thermo-formable fiber of having a second melting temperature range which is lower than the first melting temperature range to such an extent that the structural fiber does not melt in the second melting temperature range of the thermo-formable fiber, according to the preamble of the first claim.

In order to be suitable for use in immobilization devices for supporting, stabilizing or immobilizing a limb, joint, muscle, bone or other body part, a material should meet certain requirements. On the one hand the material must be sufficiently rigid, resistant to impact and compression in order to provide good immobilization and minimize the possibility of the body part enclosed by it, to move. In specific applications, such as fractionated medical diagnostic and treatment procedures, for example in radiation oncology, accurate and reproducible positioning and re-positioning of the body part are a pre-requisite to ensure that the radiation is delivered exactly at the target position where it is needed, while minimizing the risk to exposure of surrounding healthy tissue. On the other hand the material should be light and comfortable to wear, be skin friendly, provide cushioning and show some breathability to permit air and moisture transport from the skin through the material to improve comfort to the patient and minimize the risk to skin damaging or wounding. Improved comfort may be obtained by using a perforated material or by covering the inner face of a rigid brace with textile to improve the wearing comfort to the patient, provide cushioning, softness, skin friendliness, moisture handling and breathability. Furthermore, it is important that the material for the immobilization device has a sufficiently high melt strength to permit molding in the molten state, that it is sufficiently elastic and flexible during molding in order to achieve a good fit for a wider range of body sizes and shapes, and at the same time provide the right amount of support and compression.

In practice, immobilization devices are often offered as off the shelf, custom modified and custom made products. The off the shelf products are usually available in the form of pre-cut sheets of several standard sizes, they may be made adjustable, those which are made of low melting temperature material can be re-molded. Immobilization devices made of high melting temperature polymers cannot be directly fitted onto the body part, and as a consequence offer a less accurate fit. Immobilization devices which may be custom-modified are usually pre-shaped, depending on the material used they can be re-shaped by thermoforming directly on the body part to be immobilized.

DESCRIPTION OF THE PRIOR ART

WO2005052235 discloses a spacer fabric with a skin friendly inner surface, cushioning properties and built-in stiffening properties. The stiffening properties are implied by the presence of hybrid yarns, which contain 30-98% of thermoplastic melting fiber and 2-70% of structural fiber. The structural and thermoplastic fiber are closely commingled in at least part of one of the outer layers of the spacer fabric. Heating of the spacer fabric to a temperature of 180-300° C. causes the thermoplastic material to melt and to wet out. Upon subsequent cooling a matrix of thermoplastic material is formed which stiffens the surface of the spacer fabric and entails a loss of the porosity of the fabric. Suitable thermoplastic materials include polyester, polyamide, polypropylene, polyethylene, polyurethane, polyvinylchloride or rubber based materials, those which are mouldable at a temperature between 70-90° C. being preferred. Suitable materials for use as structural fibers include natural or regenerated fibers such as cotton or viscose. The hybrid yarn may comprise filament fibers or staple fibers formed into texturized, flat or spun yarn.

However upon cooling, the thermoplastic material shrinks and involves a simultaneous shrinking of the structural fiber and a density increase of the fabric, this phenomenon being particularly pronounced in case the thermoplastic fiber content of the hybrid yarn is significant. To shape the spacer fabric, the material is re-heated and shaped, and it is alleged that virtually no shrinking takes place upon re-heating. The provision of stiffening properties thus requires the use of two processing steps. Besides this, the behavior of hybrid fibers during subsequent shaping and use, the adhesion of the thermoplastic fiber to the structural fiber and the mechanical and thermo-molding properties of the crimped fibers have been found difficult to control.

EP-A-758.693 seeks to provide a plain knit fabric in which each loop is formed of threads of a first inorganic material and a second thermoplastic material which has a shape memory and is capable of binding to the first material. Both the first and second material are evenly distributed over the braiding. Suitable inorganic materials include mineral fibers, metal or ceramics. Suitable thermoplastic materials are those which have a softening temperature below the softening temperature of the inorganic material. Depending on the size of the article to be made, a plurality of layers of the above-described material may be stacked on top of each other. The fabric is converted into a half product by pre-stressing the braiding and heating it to a temperature below the melting point of the thermoplastic yarn, which then assumes the shape of the knitted fabric and ensures that the braiding keeps its shape even when removing the stresses. The half product is processed into an end product by re-heating the pre-stressed fabric it to the melting point of the thermoplastic material to permit flowing of the thermoplastic material, to achieve binding amongst the threads of the thermoplastic material and with the treads of the first material, followed by shaping into the final shape. After cooling down, a rigid end product is obtained which maintains its shape. However, the flowing of the thermoplastic material causes matrix formation to occur, gaps present in the fabric are closed and the porosity and breathability of the material is lost.

WO2006015599 discloses a three-dimensional structure of a weft knitted tubular spacer fabric for seamless fit in orthopedic products for preventive as well as for treatment purposes. The knitted spacer fabric comprises a first outer layer and a second outer layer made of a yarn comprising Elastane, polyester, polyamide, polypropylene, wool, cotton or viscose or a combination thereof, and an intermediate spacer layer integrated with the first and second outer layers. The pile yarns of the intermediate spacer layer may comprise polyester, polyamide, polypropylene, wool, cotton or viscose or a combination thereof. The spacer fabric is suitable for use in bone fracture stabilization, orthopedic splints, casts and bracings, prosthetic limbs or devices, orthopedic soft goods and supports as well as sports bracing and sports goods equipment and work wear. The material may be shaped by means of thermo-shaping, molding, heat setting, shrinking, shaping on/in a mould, etc, but cannot be directly molded onto a patient at low temperature.

EP-A-003.845 discloses orthopedic splints and the like which are made of a bandage comprising a web and a fibrous filler material which is impregnated with a cross-linked copolymer of lactone and acrylate monomers. The material is moulded by heating the sheet to a temperature above the softening point of the copolymer, shaping it and having it cooled to a rigid state. However, the liquid impregnation reduces the softness, drapeability, flexibility and elasticity of the fabric materials before thermoforming. Besides that, with the used impregnation techniques there is a significant risk that impregnation is limited to the surface of the fibrous material and does not extend into the web, and that voids originally present in the web become partly or entirely closed. This has an adverse effect on the homogeneity of the mechanical properties, the permeability and breathability of the material.

EP-A-1.582.187 discloses an immobilization device made of a perforated sheet of a thermoplastic material to permit moisture evaporation from the skin and provide air permeability. The thickness of the material mostly varies between 0.5-5 mm, preferably between 1-4 mm depending on the envisaged rigidity and stiffness, and on the porosity or number and size of the perforations present. Although perforations are present, the material is still relatively rigid and thus uncomfortable, an immobilization device made of it may be heavy and thick and thus uncomfortable to the wearer, and its permeability to moisture and air is still limited. The consequence is that warming up and moisture accumulation on the skin cannot be avoided, which may lead to skin maceration and skin breakdown. To improve comfort to the patient the side of the sheet contacting the skin can be partly covered with a soft material.

U.S. Pat. No. 5,487,803 discloses a pliable knitted article in which a metal yarn is combined with a plastic yarn into a combined yarn which is knitted in such a way that one of the faces of the knitted fabric consists predominantly of the metal yarn and the other face consists predominantly of the plastic yarn. Preferred plastic yarns include those which are textured or elastic for example Lycra, to permit stretching them while knitting and in that way adapting the density. The knitted article is combined with a sheet of a plastic material to provide a composite article which is reinforced with a metallic structure.

EP-A-310.200 discloses a composite article in which filaments having different melting or decomposition points are combined into a yarn, a woven fabric or knitted fabric and/or non-woven material. By heating the combined filament to a temperature above the melting point of the low melting filaments which preferably is maximum 135° C., and below the melting point of the high melting reinforcing filaments which preferably is at least 145° C., the material of the low melting filaments flows out to form a matrix in which the reinforcing filaments are embedded and fixed in pre-determined positions. Usually an article with a closed surface and hardly or no breathability properties is obtained. Suitable materials for use as high melting filaments include highly drawn polymer yarns with a tensile strength of more than 2 GPa, for example polyethylene, polypropylene homo- or copolymers. Suitable materials for use as the low melting filaments are polymers with low molecular weight and drawn to a small extent.

EP-A-887.451 discloses a knitted fabric presenting a satin-like surface feel, which can be molded by heat setting for use in breast cups for women's brassieres. The warp knitted fabric comprises a first set of yarns providing a satin-like surface effect which are interknitted with a set of monofilament partially oriented polyester ground yarns forming a stabilizing fabric ground structure. Preferably a set of elastic yarns is inlaid with the satin-effect and the ground yarns. The ground yarns show a high degree of elongatability and a high degree of shrinkability of about 9-15% such that when exposed to heat, the ground yarns will collapse to conform to the mould. Thereby the yarns are permanently set into the moulded shape. The elastic yarns predominantly serve the function of contracting the knitted structure of the fabric, in particular of the satin-effect yarns in the relaxed state of the fabric so as to impart a more compacted stitch density than would be achievable by warp knitting of the ground and satin-effect yarns alone.

DESCRIPTION OF THE INVENTION

It is the aim of the present invention to provide a hybrid fabric, which may be directly molded onto the patients' body, which shows good breathability to both moisture and heat after having been molded and which provides improved comfort to the patient while providing sufficient immobilization.

This is achieved according to the present invention with a hybrid fabric showing the technical features of the characterizing portion of the first claim.

Thereto, the hybrid fabric of this invention is characterized in that the hybrid fabric comprises
(1) a first network comprising the structural fibers,
(2) a second network comprising the thermo-formable fibers, the thermo-formable fibers comprising non-relaxed fibers made of a thermoplastic material, and
(3) a plurality of openings between the fibers of the first and second network, the hybrid fabric further being characterized in that the structural and thermo-formable fibers of respectively the first and second network interpenetrate one another and are connected to each other over at least part of the first and second network at a plurality of knot positions in the fabric where the structural and thermo-formable fibers are interwoven.

From the above it can be understood that the hybrid fabric of this invention is thermo-formable.

The wording "knot" is meant to include those positions where the fibers of the first, respectively the second network are connected to each other and the positions where the fibers of the first network are connected to the fibers of the second network. Often at those positions the fibers are bent and form loops which are entangled, the fibers combine into a knot-like configuration or into a stitch. Thus a knot is understood to include a knot, stitch or loop or an equivalent configuration wherein the structural and/or thermo-formable fibers are inter-woven or assembled.

The hybrid fabric of this invention can be produced by different methods as long as they provide the possibility of having at least part of the fibers of the first and second network connected to each other at a plurality of knots. Or in other words, the hybrid fabric of this invention can be produced by any method in which interconnected loops or stitches of the structural and thermo-formable fibers are provided. Examples of suitable methods include knitting, braiding, weaving and any type of methods considered suitable by the person skilled in the art for the production of woven fabric, but preferably use is made of the technique of knitting. Although different techniques for braiding, knitting and weaving exist, where the fibers are processed in different patterns, most of them will be suitable for use with the present invention and the skilled person will be capable of choosing the most appropriate fabric taking into account the nature of the application of the fabric.

Moulding of the thermo-formable hybrid fabric of this invention into the appropriate form or article is achieved by heating the fabric to a temperature which is equal to or above the second melting temperature range of the thermo-formable fiber, but below the first melting temperature of the structural fiber. The inventors have observed that such a heating causes melting of the non-relaxed thermo-formable fiber, which in an initial stage is associated with a controllable degree of shrinking of the fabric. However, short after the initial shrinking, a re-expansion of the fabric may take place. This limited, controllable shrinking is attributed to the presence of non-relaxed thermo-formable fibers and is advantageous as it permits making an article based on already prefabricated patent which keep the same shape and sizes during heating at molded temperature.

After having been heated, at the position of the knots of thermo-formable and structural fibers or thermo-formable fibers only, apparently the thermo-formable fibers are capable of pulling the knot forming fibers together, in other words they are capable of decreasing the dimensions of the knot. As a result, upon cooling, the majority of the consolidation of the thermo-formable material is observed at the position of the knots. At the position of the fibers, i.e. the parts of the fibers extending between the knots, the initial shrinking of the fabric induced by the shrinking of the thermo-formable material is counteracted by the rigidity provided by the structural fibers with the thermo-formable fibers in the softened state induces re-expansion of the network of the structural fibers and thus of the fabric. This way, stresses occurring in the material by the shrinking of the thermoplastic fibers disappear and relaxation of the structural fibers and hybrid fabric itself may take place, thus releasing any unwanted remaining internal stress from the fabric. This is in contrast to hybrid fabrics known from the art, where melting of the thermoplastic fibers results in collapsing of the structure. The thermo-formable hybrid fabric of this invention provides the additional advantage of being re-moldable several times, simply by re-heating the fabric to melt the thermoplastic monofilament fibers, shaping the fabric and leaving the fabric to cool in the desired shape. After this re-heating and subsequent cooling, negligible shrinking is observed. Because consolidation of the fabric upon cooling of the interpenetrating networks is concentrated at the position of the knots, the first and second networks get connected to form a unity, thereby affecting the open spaces which occurred in the hybrid fabric before heating, to a limited extent. After consolidation, a fabric is obtained in which the distribution of the structural and thermo-formable fibers is hardly changed as well as the molding and mechanical properties. Thus a thermo-formable hybrid fabric may be provided with isotropic molding and mechanical properties, depending on the distribution of the structural and thermo-formable fibers in the fabric.

From the above it should be clear that the thermoplastic fibers in the hybrid fabric of this invention provide the possibility to mould the fabric into any desired shape. The structural fibers on the other hand function to provide sufficient rigidity and melt-strength in the molten state of the thermoplastic fibers, and to improve the rigidity and stability of the hybrid fabric after moulding.

The thermo-formable hybrid fabric of this invention may consist of a first network comprising structural fibers and a second network comprising non-relaxed thermo-formable fibers. However, if so desired additional interpenetrating networks of structural and non-relaxed thermo-formable fibers may be added. Thus the thermo-formable hybrid fabric of this invention may take the form of a two- or three dimensional network. The first network may comprise one single type of structural fibers or a combination of structural fibers of different origin. The second network may comprise one single type of non-relaxed thermo-formable fibers or a combination of two or more non-relaxed thermo-formable fibers of different origin. The structural and non-relaxed thermo-formable fibers may be homogeneously distributed over the fabric if a thermo-formable fabric with homogeneous and isotropic behavior in the melt is envisaged. However, depending on the envisaged application it may be desirable to locally increase the concentration of structural or non-relaxed thermo-formable fibers. This way, shrinking behaviour may be controlled and locally altered.

The non-relaxed thermo-formable fibers may take the form of monofilament fibers, multifilament yarns, twisted fibers consisting of one type of thermo-formable material or of a combination of different types of thermoplastic materials. However, the use of monofilament fibers is preferred as they have a higher material density and provide an improved interpenetration of the networks of the structural fibers and the thermoplastic fibers. The use of non-relaxed monofilament thermo-formable fibers permits obtaining a fabric the properties of which may be better controlled upon thermo-forming, with an improved melt strength and improved structural and mechanical homogeneity of the material in use. The thermo-formable, non-relaxed fiber is preferably made of a thermoplastic material selected from the group of polyesters for example poly-ε-caprolactone; polyurethane; trans-polyisoprene; a blend of one of these materials with another polymer for example a blend of a polyester or poly-ε-caprolactone with different polymers; copolymers or blends or combinations of two or more of these materials; and thermoplastic elastomers, such as for example polyolefin elastomers or thermoformable nanocomposites. Besides the above mentioned materials some of the polyolefins having side chains of cyclic hydrocarbons, show the combination of a sufficiently low melting or softening temperature and sufficient softness and flexibility after cooling and crystallization. thermoplastic elastomer, which thermoplastic elastomer is a copolymer of ethylene with at least one α-olefin having 3-10 carbon atoms, or a blend of two or more of such copolymers. Other preferred plastic material include those comprising an amount of a thermoplastic elastomer which is a copolymer of ethylene with one or more α-olefins having 3-10 carbon atoms, more preferably a copolymer of ethylene with 1-butene or a copolymer of ethylene with 1-octene or a blend of two or more of these copolymers. These are particularly preferred because they are transparent.

The person skilled in the art will be capable of selecting the most appropriate thermoplastic material having a melting point below 100° C. from the available thermoplastic materials. Preferred are non-relaxed, at least partly oriented monofilament thermoplastic fibers, more preferred non-relaxed oriented monofilament poly-ε-caprolactone fibers, in particular non-relaxed monofilament fibers of partially cross-linked poly-ε-caprolactone. This material presents the advantage of having a low melting range (60-70° C.) and of being still moldable at temperatures above its crystallization temperature, in particular up to 40-45° C., so that a large temperature interval is available for molding the material at body temperature. This material presents the additional advantage that in the molten state, superimposed layers show good adhesion to one another.

The structural fibers used in the hybrid fabric of this invention may be used in the form of monofilament fibers, multifilament yarns or twisted of twined yarns consisting of one or more different types of structural fibers.

Suitable structural fibers for use in the hybrid fabric of this invention include inorganic fibers such as glass fibers, ceramic fibers, basalt or metal fibers, natural or regenerated fibers such as cotton and flax, but also viscose or carbon fiber or synthetic organic fibers or fibers made of a thermoplastic material with a melting temperature-range that is substantially above the melting temperature range of the thermo-formable fibers such as modified or non-modified polyester, Kevlar, polyamide, polypropylene, polyethylene, polyurethane, polyvinylchloride or mixtures of two or more of the afore mentioned fibers. In case the structural fibers are made of thermoplastic material, the lower temperature of their melting range should preferably be at least 25° C. above the higher temperature of the melting range of the thermoplastic material.

If so desired, either the fabric, the structural fibers or the thermo-formable fibers may be coated to imply preferred properties to the material. For example a coating may be applied to inhibit sticking of superimposed sheets of fabric.

For the structural fibers as well as the non-relaxed thermo-formable fibers preferably use is made of continuous fibers as they provide a softer feeling. A hybrid fabrics produced using the above-described materials is soft and flexible before a heating treatment is carried out, it may be processed in an easy way, joining of end parts is easy and it may be handled as an ordinary textile material. The hybrid fabric can be processed into any desired shape or form before thermoforming using clothing sews technology.

The preferred thermo-formable fiber is non-relaxed poly-ε-caprolactone having a residual elongation at stretching at 60° C. under constant load of between 30 and 120 mm. The residual elongation at stretching in longitudinal direction of the fibre is preferably between 50 and 100 mm in longitudinal direction. Residual elongation at stretching (RES) is measured by subjecting a standard sample fiber having a length of 25 mm, to a constant load of 0.3 g at 60° C., and by measuring the length under load at room temperature. The residual elongation at stretching is related to the melt strength and varying the melt strength permits varying the drape, shape memory and mouldability of the thermoplastic melting material.

The thermoplastic melting material and the hybrid fabric incorporating this material can vary from very soft, ductile, low shrinking, low shape memory to less ductile, high shrinking, high shape memory. A fabric incorporating this kind of thermoplastic fibers is thermoformable, flexible, easily drapeable and can be positioned in a simple manner to conform in an optimum way to the body part that needs to be immobilized so that molding is facilitated. Formability or mouldability of the fabric is provided by the matrix of the thermoplastic fibers, whereas structural support in the molten state of the thermoplastic fibers and after cooling at room temperature is provided by the network of the structural fibers. With the thermoplastic material in the molten state, the material shows adhesive properties and end parts of the fabric can be connected, by contacting the end parts in an overlaying manner and exerting some pressure, without the need to use an additional adhesive.

The preferred non-relaxed thermo-formable fibers have a diameter of between 80 and 175 μm, more preferably between 100 and 150 μm.

By carefully selecting the nature of the non-relaxed thermoplastic fiber, and type of the pattern of the first and second network which are knitted, woven or braided, the connection pattern between the first and the second network and the number of connections, the number and dimensions of the knots, the degree of shrinking of the hybrid fabric of this invention can be controlled.

The hybrid fabric of this invention is thermoformed into an immobilization device by heating the fabric to a temperature which corresponds to or is slightly above the melting range of the thermoplastic fiber. In case non-relaxed, partially cross-linked poly-ε-caprolactone is used, heating to a temperature between 60 and 70° C. suffices to melt the thermoplastic fiber, without melting the structural fiber. After a first initial shrinking is observed, the fabric relaxes and expands again, while structural support for the molten network of thermoplastic fibers is provided by the network of the structural fibers. The poly-ε-caprolactone may be shaped, molded and re-molded after melting at 60-65° C. at a temperature to 40-45° C. and is thus suitable for direct molding to the human body at any temperature between the melting point to above the crystallization point. The inventors have observed that with the thermoplastic or poly-ε-caprolactone fiber in the molten state, the fabric is drapeable, but nevertheless maintains its structure and coherence. This property is attributed to the partly cross-linking of thermo-formable fibers and presence of the structuring fiber in the fabric. The hybrid fabric is draped over the body part that needs to be immobilized, with the thermoplastic fiber in the molten state, shaped to conform and to fit to the body part needed to achieve the desired degree of immobilization and left to cool. Cooling involves crystallization of the thermoplastic material, which is associated with hardening and some degree of shrinking of the thermoplastic material. The shrinking extends to the whole material of the hybrid fabric and results therein that an improved fit to and improved immobilization of the body part to be immobilized is achieved. In case re-molding is required, the thus molded fabric may be re-heated and draped to conform to the part that needs to be enclosed by the fabric.

The hybrid fabric of the present invention has a limited thickness as compared to the conventionally used sheets of thermoplastic material used in the production of immobilization devices. Whereas the fabric of this invention will usually have a thickness of between 0.5-2 mm, often about 0.8-1.5 mm, poly-ε-caprolactone sheets usually have a thickness of at least 1.6 mm. After thermoforming at a temperature of between 60 and 65° C., the thickness of the molded fabric will usually be between 0.5 and 2 mm, preferably between 0.8 and 1.5 mm. Thus, the present invention permits producing immobilization devices with a reduced thickness and weight, with improved wearing comfort. Thickness of the hybrid fabric of this invention is measured using a micrometer or gauge instrument.

Preferred hybrid fabrics for use within the scope of the present invention are those with a degree of shrinking after being molded at a temperature of between 60-65° C., of between 0 and 30%, in longitudinal and transversal direction. The degree of shrinking shown by the hybrid fabric of this invention upon melting and crystallization may be adjusted by the choice of a suitable fabric design and by adjusting the concentration of the thermoformable melting fiber. Therefore, the hybrid fabric of this invention will usually contain between 60 and 98% by weight of thermo-formable fibers and between 40 and 2% by weight of structural fibers. Support in the molten state and at room temperature of the thermoplastic fibers will be higher or lower, depending on the concentration and mechanical properties of the structural fibers.

The rigidity, degree of fixation and stability of an immobilization device obtained after thermoforming, made of the hybrid fabric of this invention may be varied by varying the concentration of structural fibers in the hybrid fabric. Thus, immobilization devices of widely varying immobilization ability may be provided. Thereby the immobilization device may vary from a device which in the molded state is quite flexible and provides some support, to a rigid immobilization device which effectively restrains the movability of the body part enclosed by it. This is important in particular when used to fix the position of a body part in radiation therapy or diagnostics, or when exposing a patient to fractionated treatment. In such cases precise positioning and highly accurate, reproducible re-positioning of the target and surrounding normal structures of the head is a pre-requisite to ensure that the radiation is delivered exactly at the target position where it is needed, while minimizing the risk to exposure of surrounding healthy tissue. The immobilization device made by molding the hybrid fabric of this invention shows the required dimensional stability needed to immobilize a body part.

Preferred non-relaxed thermo-formable fibers are those showing shrinkage of between 50-80% after having been heated to 65° C. to provide optimum consolidation of hybrid fabric and fit after molding. The degree of shrinking of thermo-formable fiber is measured by heating a sample with an initial length Lo of 100 mm to 65° C. in a water bath for 1 minute. Thereafter, the sample is left to cool at room temperature and the length Lh is measured. The degree of shrinking is calculated as follows: $((L_o-L_h)/L_0) \times 100$. The degree of shrinking of a piece of fabric is determined in the same way, using a piece of 10×10 cm.

Particularly preferred thermoplastic fibers have a shape memory of between 45 and 98%. A fabric incorporating such thermoplastic fibers may be re-used several times, while it will always return to a shape close to the former shape as regards from and dimensions, and maintain its adhesive properties. The melt memory is determined by measuring the recovering of the length of thermoformed poly-ε-caprolactone fiber after stretching to 200% at 65° C., cooling at 20° C. and reheating above melting temperature of 65° C. The melt memory designates the ratio (length before stretching–length after stretching to 200% at 65° C., cooling at a fixed position at 20° C. and reheating above melting temperature of 65° C. and cooling again at 20° C.)/(length after stretching to 200% at 65° C., cooling at a fixed position at 20° C. and reheating above melting temperature of 65° C. and cooling again at 20° C.).

The hybrid fabric of this invention preferably has a density of between 0.5 and 0.8 $g/cm^3$ after thermoforming at a temperature of between 60-65° C.

The hybrid fabric of this invention preferably has a bending modulus of between 70 and 320 MPa after thermoforming.

The hybrid fabric of this invention may be used in combination with a sheet of thermo-formable material, such as the materials disclosed in EP1854439 and EP1582187 which are hereby incorporated by reference. Other suitable sheet materials include those which comprise at least one thermoplastic elastomer, which is a copolymer of ethylene with at least one α-olefin having 3-10 carbon atoms, or a blend of two or more of such copolymers. Preferred plastic material include those comprising an amount of a thermoplastic elastomer which is a copolymer of ethylene with one or more α-olefins having 3-10 carbon atoms, more preferably a copolymer of ethylene with 1-butene or a copolymer of ethylene with 1-octene or a blend of two or more of these copolymers.

In that case, usually the hybrid fabric will be fastened to the sheet of the thermoformable material. Such an article may comprise a first layer of the above-described hybrid, fastened on top of a second layer of a thermo-formable polymer sheet material, although sandwich structures may be envisaged as well. According to another embodiment, a sample of the above described hybrid fabric may be fastened along its edges to a thermo-formable sheet material.

The present invention also relates to a method of producing an immobilization device wherein the above-described hybrid fabric is heated to a temperature of between 60 and 70° C., shaped and left to cool. Heating of the hybrid fabric of this invention with the purpose of molding it into a form may be done by means of for example an infrared or near infrared oven or microwave oven or in a hot water bath or hot air or any other suitable way of heating. After having been processed into an immobilization device, the immobilization device may be re-molded to a different shape or size by re-heating and re-shaping the material and leaving it to cool.

The hybrid fabric of this invention shows several advantages. Whereas the thermoplastic fibers provide the moldability, the structural fibers give structure and support to the fabric and contribute to increasing the rigidity and stability of an immobilization device molded from such a fabric, already provided by the thermoplastic material. The above-described hybrid fabric as well as a part obtained by molding the hybrid fabric of this invention, show good permeability, in particular good breathability and moisture handling properties, such as moisture permeability through the material thickness. This is due to the fact that porosity and open spaces present in the hybrid fabric before heat treatment, are reduced to a limited extent only. Moreover by careful selection of parameters, the reduction of the permeability may be controlled. Evaporation of moisture from the skin enclosed by an article molded from the hybrid fabric of this invention is permitted and heat exchange between the skin and the environment may take place. The permeability is provided by the presence of open spaces between the structural and the thermoplastic material fibers. Because of these properties, the hybrid fabric of this invention is suitable for use in a wide variety of applications, for example immobilization devices, sports dresses, and for use in sports applications such as for example protective plates or parts or shoe insole and gloves. A conventional sewing technique can be used for adding a zip type of fixation to a hybrid fabric. Examples of immobilization devices include the production of orthopedic support products for the different body parts, such as knee, foot, wrist, back, neck, elbow, shoe insole, etc. which need to be adjustable as regards shape and size, or may need to be re-molded after a certain time. Re-molding can be done by heating the molded fabric to the melting temperature of the thermoplastic material, i.e. a temperature between 60 and 65° C. and re-molding the fabric. The hybrid fabric of this invention is also suitable for processing into immobilization devices for patient fixation in radiation oncology which shows better transmission factor for X-ray and high energy particles (ions, protons) due to the low density.

FIG. 1 is a schematic drawing of a part of the hybrid fabric of this invention. The hybrid fabric comprises a first network of structural fibers 1, which interpenetrates the second network of thermo-formable fibers 2. The first and second network are connected to each other at the position of loops 3, knots, stitches, in other words positions where the fibers are bent and interwoven. The remaining parts of the thermo-formable fibers and structural fibers may run along each other or extend in a random way in two or three dimensions, they may extend straight or be bent.

The invention claimed is:

1. An immobilisation device for immobilizing a body part in a certain position, the immobilization device comprising:
   a hybrid woven or knitted fabric, comprising at least one structural fiber having a first melting temperature range and at least one thermo-formable fiber having a second melting temperature range which is lower than the first melting temperature range to such an extent that the structural fiber does not melt in the second melting temperature range of the thermo-formable fiber, wherein the hybrid fabric comprises:
   (1) a first network comprising the structural fibers,
   (2) a second network consisting of the thermo-formable fibers, and
   (3) a plurality of openings between the fibers of the first and second network, wherein the structural and thermo-formable fibers of respectively the first and second network interpenetrate one another and are connected to each other over at least part of the first and second network at a plurality of subsequent loops,
   wherein the hybrid fabric has a density of between 0.5 and 0.8 g/cm$^3$ after thermoforming at a temperature of between 60-65° C., and
   wherein the at least one thermo-formable fiber is a non-relaxed monofilament fiber of partially cross-linked poly-ε-caprolactone being moldable at temperatures up to 40-45° C.

2. The immobilisation device as claimed in claim 1, wherein the at least one thermo-formable fiber has a residual elongation at stretching of between 30 and 120 mm.

3. The immobilisation device as claimed in claim 1, wherein the at least one thermo-formable fiber has a diameter of between 80 and 175 µm.

4. The immobilisation device as claimed in claim 1, wherein the at least one thermo-formable fiber is an oriented poly-ε-caprolactone fiber.

5. The immobilisation device as claimed in claim 4, wherein the poly-ε-caprolactone fiber shows a shrinkage of between 50-80% after having been heated to 65° C.

6. The immobilisation device as claimed in claim 4, wherein the poly-ε-caprolactone fiber has a melt memory of between 45 and 98%.

7. The immobilisation device as claimed in claim 1, wherein the fabric has a thickness of between 0.5 and 2 mm, after thermoforming at a temperature of between 60 and 65° C.

8. The immobilisation device as claimed in claim 1, wherein the degree of shrinking of the fabric at a temperature of between 60-65° C. is between 0 and 30%, in longitudinal and transversal direction.

9. The immobilisation device as claimed in claim 1, wherein the hybrid fabric contains between 60 and 98% by weight of the at least one thermo-formable fiber and between 40 and 2% by weight of structural fibers.

10. The immobilisation device as claimed in claim 1, wherein the hybrid fabric has a bending modulus of between 70 and 320 MPa at room temperature after thermoforming at a temperature of between 60-65° C.

11. The immobilisation device according to claim 1, wherein a first layer of the hybrid fabric is fastened on top of a second layer of a thermo-formable polymer sheet material.

* * * * *